United States Patent [19]

Moessner

[11] Patent Number: 4,548,051
[45] Date of Patent: Oct. 22, 1985

[54] CRYOSTAT MICROTOME APPARATUS

[75] Inventor: Gerhard Moessner, Nussloch, Fed. Rep. of Germany

[73] Assignee: Parke, Davis & Company, Morris Plains, N.J.

[21] Appl. No.: 462,748

[22] Filed: Feb. 1, 1983

[30] Foreign Application Priority Data

Feb. 3, 1982 [DE] Fed. Rep. of Germany ... 8202647[U]

[51] Int. Cl.$^4$ ............................................... F25C 5/02
[52] U.S. Cl. .......................................... 62/320; 62/258; 62/293; 62/448; 248/405; 248/669; 269/60; 269/61; 312/272; 312/306
[58] Field of Search ............... 62/514 R, 258, 293, 62/440, 448, 404, 407, 254, 255, 256, 320; 269/60, 61; 312/306, 272; 248/405 R, 656, 669

[56] References Cited

U.S. PATENT DOCUMENTS

| 1,242,110 | 10/1917 | Koken | 248/405 R |
| 3,125,811 | 3/1964 | Pierce et al. | 269/60 |
| 3,204,424 | 9/1965 | McCormick et al. | 62/320 |
| 3,228,284 | 1/1966 | Kallenberg | 248/405 R |
| 3,462,969 | 8/1969 | Grasenick et al. | 62/64 |
| 3,627,241 | 12/1971 | Santirocco et al. | 248/656 |
| 4,138,082 | 2/1979 | Fatemi | 269/60 |

Primary Examiner—Ronald C. Capossela
Attorney, Agent, or Firm—Alan H. Spencer; Stephen Raines

[57] ABSTRACT

A cryostat microtome apparatus comprises a cooling enclosure which can be set to a predetermined internal temperature and a microtome disposed in the enclosure. The enclosure is supported on a support assembly which is vertically adjustable to permit stepless adjustment of the height of the enclosure, for adaptation to operator requirements. A mechanical actuating assembly and/or a gas spring assembly is provided for height adjustment of the apparatus.

9 Claims, 7 Drawing Figures

CRYOSTAT MICROTOME APPARATUS

BACKGROUND OF THE INVENTION

The present invention relates generally to a cryostat microtome.

A cryostat microtome comprises for example a thermally insulated cooling chamber which can be set to a predetermined low temperature by means of a refrigeration unit and which is carried on a support assembly. Disposed in the cooling chamber or enclosure is the microtome apparatus itself. Such arrangements suffer from little or no formation of frozen fog or rime therein, when dealing with objects requiring to be processed by the microtome.

In such microtomes, the cooling enclosure with the microtome integrated therein is supported on a support assembly at a height which permits the arrangement to be operated by an operator either in a sitting position or in a standing position. However, microtomes are pieces of precision equipment for making very thin sections (1 to 15 $\mu$m) from hard or frozen tissues and they are often used in particular for making thin sections which are referred to as series sections, that is to say, a series of sections taken from the tissue in question, without gaps or intervals between the sections produced. It will be appreciated that operating such microtomes requires a high level of attention and concentration, so that it is important for the microtome to be in the best possible position relative to the operator.

SUMMARY OF THE INVENTION

An object of the invention is to provide a cryostat microtome apparatus such that operation of the microtome is facilitated from the point of view of the operator.

Another object is to provide such a microtome which permits the operator to be in the best possible position relative to the microtome.

A further object of the invention is to provide a cryostat microtome apparatus which can be used by an operator in a sitting or in a standing position.

Yet another object is to provide a cryostat microtome apparatus which can be readily adapted to the differing requirements of different operators.

A still further object of the invention is to provide a cryostat microtome which provides for stepless adjustment to the varying sizes of operators.

Yet a further object of the invention is to provide an adjustable cryostat microtome apparatus in which heightwise adjustment of the microtome to adapt it to operator requirements is effected in a uniform manner such that the microtome remains level throughout its adjusted positions.

Still another object of the present invention is to provide a cryostat microtome which is capable of finely controllable adjustment of the microtome positioning for adaptation to operator requirement.

These and other objects are achieved in a cryostat microtome apparatus comprising a cooling or refrigerating chamber which can be set to a predetermined low temperature by a refrigeration unit, and a microtome within the chamber. The chamber with microtome therein is carried adjustably in respect of height on a support assembly, preferably steplessly.

It will be seen therefore that the apparatus according to the principles of the present invention can be readily and preferably steplessly adjusted to the height of the operator, whether in a sitting position or in a standing position, in order to give optimum working conditions for operation of the microtome. If desired, the height of the microtome can be adjusted to finely adapt it to the height of the respective operator, while the operator is actually in the process of using the microtome in the cooling chamber.

As indicated, in an advantageous embodiment of the invention, the cooling chamber with microtome therein is preferably steplessly adjustable in height relative to the surface on which the apparatus stands. Various operating assemblies may be employed in order to provide for the height adjustability of the apparatus, as will become apparent hereinafter.

In one aspect of the invention, the support assembly comprises a base frame for mounting the microtome apparatus on a suitable support surface, and a support frame structure which is connected at its lower end to the base frame of the apparatus and at its upper end to the cooling chamber enclosure, the support structure comprising mutually relatively movable components thereby to permit adjustment in height of the apparatus.

The base frame structure may comprise a right-angled quadralateral structure, that is to say, a square structure or a rectangular structure. The top surface thereof is disposed at a spacing from the bottom support surface, thereby to form at least one hollow space or chamber which is preferably enclosed by side walls extending downwardly from the top surface of the base structure. Drive and actuating means for heightwise adjustment of the apparatus can thus be accommodated in the above-mentioned hollow space in the frame structure. The frame structure may be formed for example from four hollow shaped members, such as round or square or rectangular elements, with the hollow spaces or cavities therein being in communication with each other, better to accommodate the drive and actuating means.

For the purposes of supporting the cooling enclosure, the base structure preferably comprises four perpendicular supports such as columns or pillars which are disposed generally at the corners of the square or rectangular configuration defined by the base structure. The pillars or columns reciprocally mount guide support members which are joined to the cooling enclosure. The pillars or columns and the members movable thereon therefore serve as a guide arrangement in the upward and downward movement of the cooling enclosure, and can also serve as a drive means for producing the movement of the cooling chamber.

In an embodiment of the invention, in which the columns or pillars also serve as the above-mentioned drive means for producing the upward and downward movement of the cooling enclosure, at least two of the pillars or columns are in the form of screwthreaded spindles which are then engaged by two screwthreaded sleeves secured to the cooling enclosure. The other two pillars or columns then serve only to provide a guide action. In order to provide sufficient freedom of movement for the cooling enclosure, the screwthreaded sleeves are disposed at a sufficient spacing from the underneath bottom surface of the cooling enclosure so that even in the lowest position thereof, the bottom surface thereof cannot come to bear against the upper ends of the screwthreaded spindles on the base structure. Drive wheels are secured to the lower ends of the screwthreaded spindles, for rotary drive thereof. For reasons of safety, and in regard to the appearance of the microtome, the drive wheels are preferably disposed within the base structure.

The base structure preferably also carries a drive source which is reversible in its direction of rotation, for example a motor, hand crank or the like, the output shaft of which is drivingly connected to the drive wheels on the actuating spindles.

Although it may be considered sufficient for the arrangement to have just two screwthreaded spindles, as described above, for producing the upward and downward movements of the apparatus, in which case the spindles are preferably arranged at two opposite sides of the cooling enclosure or base structure, in order to ensure that the cooling enclosure moves uniformly without the danger of assuming an inclined position, it is preferable for all four support pillars or columns to be in the form of screwthreaded spindles. Such spindles engage into screwthreaded sleeves which are disposed at a spacing from the bottom surface of the cooling enclosure, and are provided with drive wheels for suitable actuation thereof. A transmission member which is connected to the output shaft of the drive source and which may be for example a V-belt, cable or the like, can then be passed around the drive wheels which are mounted on the lower ends of the screwthreaded spindles, transversely with respect to the longitudinal centreline of each thereof. Preferably however, the drive wheels on the screwthreaded spindles and the drive wheel on the output shaft of the drive source are in the form of chain wheels which are engaged by an endless chain extending around all the chain wheels. Such a drive configuration ensures that the drive forces are transmitted without play or slip, and thus ensures finely controllable heightwise adjustment of the apparatus.

In another embodiment of the present invention, at least two support pillars or columns, which are disposed at opposite sides of the base structure, are provided on their outside surfaces with respective toothed rack configurations extending parallel to the longitudinal centreline of the respective support column or pillar. The toothed rack configurations are engaged by gears which are mounted on axes which extend transversely with respect to the longitudinal centreline of the respective support pillars or columns, the axes being carried by the cooling enclosure at a spacing from the bottom surface thereof. The gears which engage the toothed rack configurations are driven in rotation by a reversible drive means, whereby the cooling enclosure, being guided in a suitable manner on the support pillars or columns, can be moved up and down to adjust the height of the apparatus. It is preferable also in that case for all four support pillars or columns to be provided with toothed rack configurations which are then also engaged by four gears, in order to ensure uniform rectilinear movement of the cooling enclosure with the microtome therein.

The drive source with its reversible direction of drive rotation and which once again can be formed by a motor, a crank or the like, is coupled by way of transmission members to the two or four gears referred to above. If the arrangement has four such gears, there being one gear associated with each of the four support pillars, each pair of gears which are disposed on the same side of the base structure are interconnected by a drive chain, while two such gears which are disposed on opposite sides of the base frame are connected by a shaft. When the arrangement has only two gears, at opposite sides of the base structure, those two gears are connected simply by means of the shaft, and the chain drive connection is omitted as there are no gears to be connected by the chains.

The four gears, the drive source and the above-mentioned transmission members may be carried on a frame assembly which is connected to sleeve members which engage over the support pillars or columns on the base structure, and which are secured to the cooling enclosure coaxially with respect to the support pillars or columns. The frame assembly is preferably of a completely or substantially closed configuration in order to exclude the possibility of the operator being put at risk of injury by the moving drive members, in order to enhance the appearance of the microtome and in order to prevent active fouling of the drive, for example by lubricants, as well as passive fouling, for example due to the ingress of foreign bodies.

Another preferred embodiment of the construction for producing the infinitely variable adjustment of the height of the microtome apparatus comprises the provision of a respective gas pressure spring on opposite sides of the microtome apparatus, between the base structure and the bottom surface of the cooling enclosure. The force exerted by the gas springs, which will preferably be arranged at least substantially vertically, is about 50 to 100N greater than the mass of the cooling enclosure, which is to be moved.

Such a spring arrangement may also be used in the abovedescribed constructions, one comprising the drive wheels on the lower ends of the screwthreaded spindles and the other comprising the assembly of toothed rack configurations and gear wheels engaging therewith. When using such a combination of spring and drive means, the drive means may then be of a less robust construction and the actuating force required on the part of the operator for the purposes of adjusting the height of the apparatus may be less, in consideration of the force applied by the spring arrangement. The force of the spring arrangement in such a combination may be less than the force of the spring arrangement when used alone.

It may be advantageous for the apparatus to include a detent or retaining means for securing the cooling enclosure with microtome therein at the desired height, particularly when the apparatus has the gas springs for producing heightwise adjustment.

BRIEF DESCRIPTION OF THE DRAWINGS

Further features and advantages of the apparatus according to the present invention will be apparent from the following description of preferred embodiments, with reference to the accompanying drawings in which.

DESCRIPTION OF PREFERRED EMBODIMENTS

Figure 1:
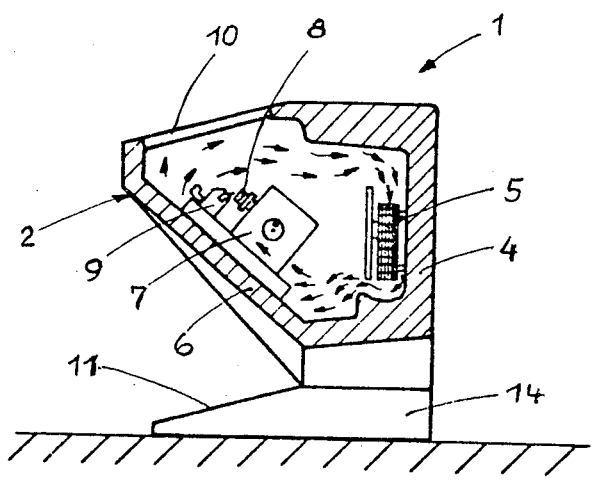
FIG. 1 is a diagrammatic view in cross-section of the basic construction of a cryostat microtome, showing the cooling enclosure or chamber which accommodates the microtome and which in turn is vertically adjustably carried on a support assembly.

Referring firstly to FIG. 1, a cryostat microtome apparatus 1 generally comprises a cooling or refrigeration chamber or enclosure 2 which is of a desk-like configuration and which is vertically adjustably carried on a support assembly, to be described hereinafter. As is conventional practice in cryostat microtome apparatuses, the walls defining the cooling chamber have good thermal insulation to minimise heat losses to the exterior of the apparatus. Disposed in the interior 3 of the enclosure 2 and mounted on a rear wall 4 thereof is a refrigeration unit 5 which however is only shown in diagrammatic form. Operation of the refrigeration unit 5 adjusts the interior of the enclosure 2 to a predetermined low temperature, and then maintains it substantially constant at the set temperature. Also disposed in the interior of the enclosure 2 is a microtome 7 which, in the embodiment illustrated, is mounted on a front wall 6 of the enclosure, being the wall opposite to the wall 4 on which the refrigeration unit 5 is carried. It will be seen that the front wall 6 extends at an inclined angle forwardly and upwardly from the bottom of the enclosure 2. The microtome 7 comprises an object holder 8 and a blade carrier 9, which can be inspected by way of a viewing opening 10 at the top of the enclosure 2. The opening 10 has a removable panel to permit operations to be carried out on the holder 8 and the carrier 9. A substantially uniform temperature is maintained in the chamber 3 in the enclosure 2, by means of the circulation of air which goes downwardly from the refrigeration unit 5 and then in a circuit within the chamber 3 of the enclosure 2, around the microtome 7, as indicated by the arrows in FIG. 1.

Figures 2, 3:
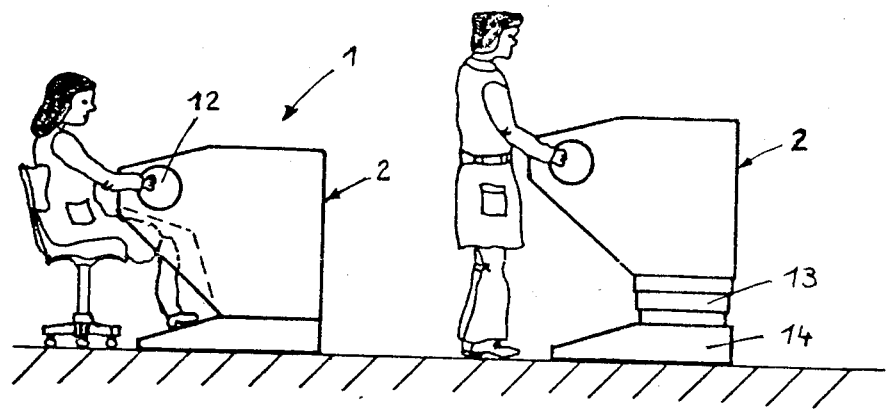
FIG. 2 shows a side view of the apparatus at a height setting for operation by a person in a sitting position.
FIG. 3 shows a view similar to that shown in FIG. 2, but with the apparatus set at a height for operation by a person in a standing position.

Reference will now be made to FIG. 2 showing the microtome apparatus 1 at the same height setting as in FIG. 1, together with an operator sitting on an operator chair. In the lower region of the front wall 6 of the apparatus 1, the enclosure 2 is provided with a space, indicated by a broken line, to receive the legs and knees of the operator. The support assembly which vertically adjustably carries the enclosure 2 has a surface arrangement as indicated at 11 in FIG. 1 (see also for example FIG. 4), on which the operator can rest his or her feet. Disposed at a side wall of the enclosure 2 is a rotary handle or knob 12, which is only indicated in diagrammatic form in FIGS. 2 and 3, for actuating the microtome 7.

FIG. 3 shows the enclosure 2 when it has been moved from the lowered position shown in FIGS. 1 and 2, into an upwardly displaced position which corresponds to the position required for operation by a person in a standing position. Heightwise adjustment of the enclosure 2 is effected by a support structure 13 which is only shown diagrammatically in FIG. 3. It will be appreciated that the enclosure 2 can be steplessly adjusted to any desired height between the positions shown in FIGS. 2 and 3 respectively, and even higher positions, whereby the apparatus can be suitably adapted to the size of the respective operator and to the respective working operations to be performed with the apparatus.

The support assembly for supporting the enclosure 2 comprises a base frame structure 14 and the support structure 13 which is connected at its lower end to the base structure 14 and at its upper end to the underside of the bottom of the enclosure 2. The support structure 13 comprises components which are movable relative to each other, for example in a telescopic-like manner, as will be described in greater detail hereinafter.

Referring now also therefore to FIGS. 4 through 7, the base structure 14 is in the form of a right-angled quadrilateral, being either a square or a rectangle. The structure 14 is shown as being of a rectangular configuration in FIGS. 4 through 7. The base structure 14 preferably has a hollow space or cavity which is enclosed by a cover panel 16 (see FIG. 5) and side plates which extend downwardly therefrom. Alternatively, the base structure 14 may have a plurality of such cavities or spaces which are defined by hollow shaped members 15 which are welded together to form the base structure, the cover panel 16 in this embodiment also closing the base structure 14 in an upward direction.

Fixedly connected to the base structure 14 are four perpendicular support members 17' in the form for example of pillars or columns while connected to the bottom surface of the enclosure 2 are guide members 18' in the form of sleeve-like members. The guide members 18' are arranged coaxially with respect to the respective pillars 17' and are reciprocal therealong.

Figure 5:
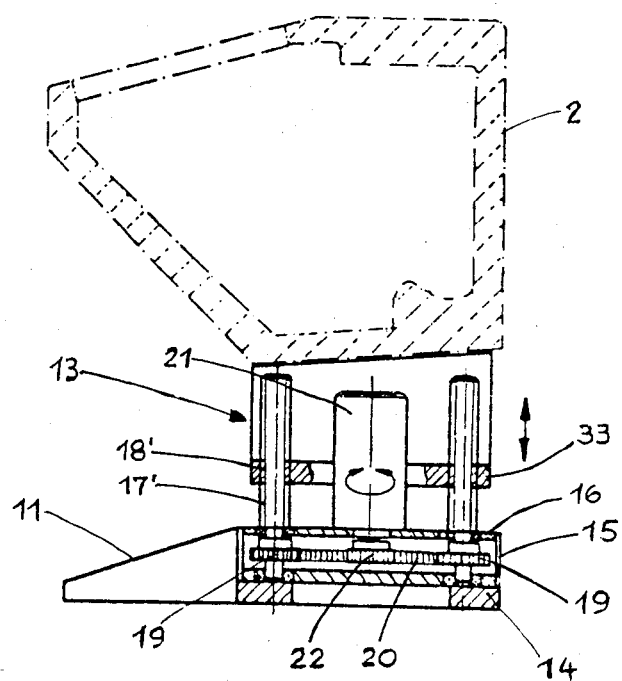
FIG. 5 shows a partly sectional view taken along line V—V in FIG. 4.

In the construction shown in FIG. 5, the perpendicular supports are in the form of screwthreaded spindles as indicated at 17', while the guide members on the enclosure are in the form of screwthreaded sleeves 18'. At least two spindles 17' are disposed at mutually opposite sides of the base structure 9, but preferably the arrangement has four such spindles 17', there being one such spindle at each corner of the square or rectangular configuration of the base structure 14.

Figure 4:
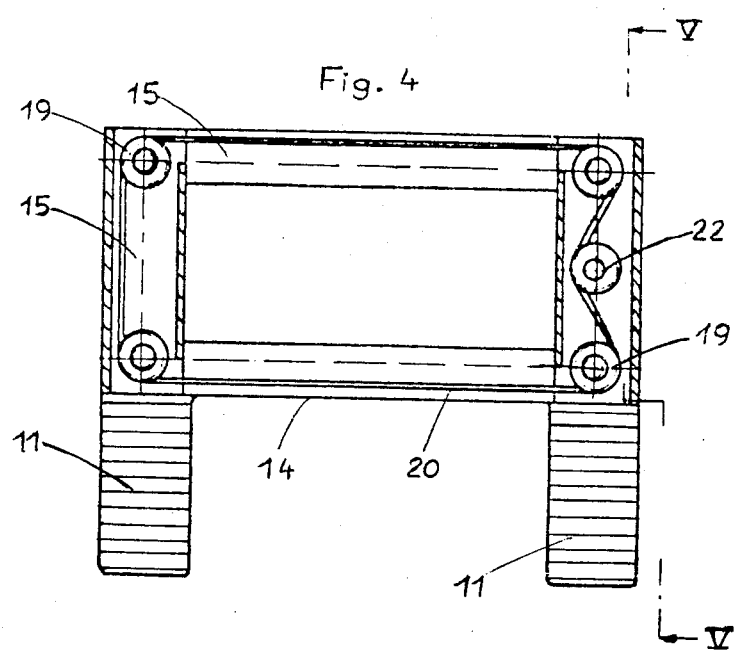
FIG. 4 shows a plan view of the base frame structure of the apparatus, shown with the top removed to illustrate the interior thereof.

At their lower ends which are disposed within the cavities or chambers defined by the hollow shaped members 15 of the base structure 14, the spindles 17' are provided with respective drive wheels 19 which, in the embodiment shown in FIGS. 4 and 5, are in the form of chain wheels and rotate the spindles 17'. Extending around the drive wheels 19 is an endless elongate transmission member in the form of an endless drive chain 20 which, as can be clearly seen from FIG. 4, extends through the spaces within all the hollow shaped members 15 of the base structure 14, the spaces in the members 15 being interconnected to permit that arrangement. The drive chain 20 is also engaged by a drive chain wheel 22 which is driven in rotation by a suitable drive source 21. The drive source 21 is shown in FIG. 5 in the form of a motor, for example an electric motor, comprising a drive output shaft on which the chain wheel 22 is mounted. The motor 21 is preferably reversible in its direction of rotation. It is also possible to use any other drive source for rotating the drive wheel 22, in place of the motor, and it is equally possible to use a different form of transmission member from the drive chain 20 illustrated, for example a belt, cable or the like, or other forms of movement transmission arrangements for rotating the spindles 19.

It will be clearly seen from FIGS. 4 and 5 that the drive wheels 19 and 22 and the drive chain 20 passing therearound are all arranged within the base structure 14 so that they themselves are protected from external influences, while however also being protected so as not to constitute the danger of injury or the like to an operator.

When the drive source 21 is rotated in one direction or the other, the spindles 17' are also rotated by way of the chain wheel 22, the chain 20 and the chain wheels 19. By virtue of the spindles 17' being engaged with the sleeves 18' which are fixed with respect to the enclosure 2, the enclosure 2 is adjusted vertically in one direction or the other, as shown by the vertical doubleheaded arrow in FIG. 5. It will be noted from FIG. 5 that the sleeves 18' are mounted to the enclosure 2 in a plate 33 which is fixedly arranged at a spacing from the bottom surface of the enclosure 2, thereby to permit the enclosure 2 to be moved downwardly into its lowermost position, without the top ends of the spindles 17' fouling the underside of the enclosure.

The support structure 13 may be clad or enclosed by a concertina-like enclosure or a telescopically displaceable apron arrangement, as indicated in FIG. 3.

Figure 6:
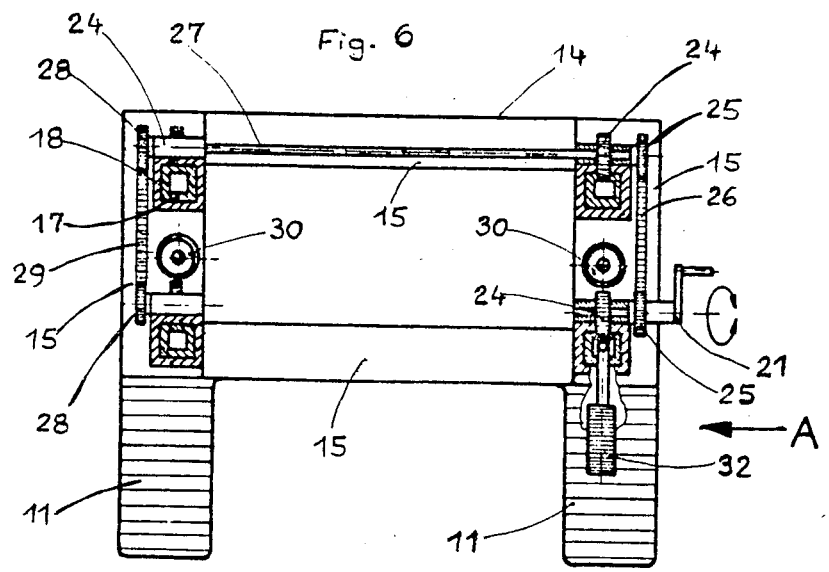
FIG. 6 shows a plan view partly in section taken along line VI—VI in FIG. 7.
Figure 7:
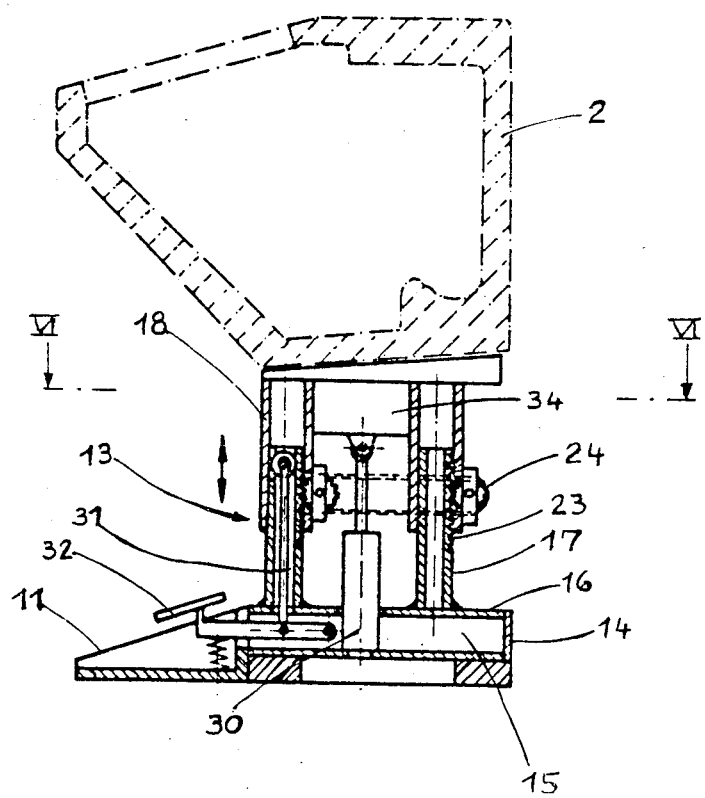
FIG. 7 shows a partly sectional view of the apparatus, viewing in the direction indicated by arrow A in FIG. 6. 1de

Reference will now be made to FIGS. 6 and 7 showing an embodiment of the apparatus which is generally similar to that shown in FIGS. 1 through 5, but with a different form of drive transmission for vertical adjustment of the enclosure 2. Thus, referring to FIGS. 6 and 7, the base structure 14 again comprises a plurality of perpendicular supports 17, there being four such supports 17 in the illustrated construction. At least two of the supports 17, which are disposed at opposite sides of the base structure 14, but preferably all four supports 17, are provided on their outside surface with toothed rack configurations 24 which extend parallel to the longitudinal centreline of the respective support pillars 17. Gears 24 which are carried by the enclosure 2 at a spacing from the bottom surface thereof engage with the respective toothed rack configurations 23. The gears 24 are driven by a reversible drive source 21 which is shown here in the form of a hand crank (see FIG. 6). The drive force is transmitted from the crank 21 by way of a gear 25 mounted on the shaft of the crank 21 and a chain 26 to a further gear 25. The two gears 25 are operatively connected to the gears 24 engaged with the rack configurations 23 on the respective supports 17. The gear assembly 24, 25 is connected by a shaft 27 which thus extends from one side of the base structure 14 to the opposite side thereof, where it connects to a gear 28 which in turn is connected to a further gear 28 by means of a drive chain 29. It will be seen therefore that, where the arrangement has four support pillars 17 each having a rack configuration 23 with an associated gear 24, the two gears arranged on each side of the base structure 14 are connected by a drive chain as indicated at 26 and 28, while two gears disposed on opposite sides of the base structure are connected by a shaft as at 27. If only two gears at opposite sides of the base structure are employed, then the shaft connection is sufficient, and the interconnection by means of chains can be omitted.

The four gears 24, chain wheels 25 and 28, chains 26 and 29 and the shaft 27 are advantageously installed in a frame which is connected to the guide members 18 which are in the form of guide sleeve members. The guide sleeve members are secured to the bottom surface of the enclosure 2 coaxially with respect to the support pillars 17 and may be additionally stiffened and reinforced by a transverse frame member 34.

FIGS. 6 and 7 also show another arrangement for stepless heightwise adjustment of the enclosure 2. The further arrangement comprises a vertically mounted gas pressure spring 30 on respective opposite sides of the base structure 14, for moving the enclosure 2 upwardly and downwardly to adjust the height of the apparatus. In that arrangement, the supports 17 are provided with externally smooth surfaces on which slide smooth inside surfaces of the guide sleeve members 18. The force of the gas springs 30 is such that it is about 50 to 100N greater than the mass of the enclosure 2 which is to be moved.

It will be appreciated that such gas springs may also be used in addition to the adjusting assemblies comprising screwthreaded spindles 17' and sleeves 18' (as described with reference to FIGS. 4 and 5) or gears 24 and rack configurations 23 (as described with reference to FIGS. 6 and 7), whereby the drive arrangement may be somewhat lighter in construction and the force required to move the enclosure 2 is also reduced. It will be further appreciated that when the gas springs are used in conjunction with the mechanical drive arrangements described with reference to FIGS. 4 and 5, and FIGS. 6 and 7 the actuating force of the springs may also be reduced, in comparison with the arrangement which uses only gas springs, without a mechanical drive arrangement.

Particularly when gas springs are used alone for adjusting the height of the apparatus, the apparatus should have an arresting or retaining means 31 for holding the apparatus at its set height, with a foot lever 32 for releasing or securing the apparatus in its adjusted position, while when the apparatus makes use of the option of also using gas springs in addition to motor-driven or manually actuated drive arrangements, such an arresting device 31 may also be an advantageous feature.

Various alterations and modifications may be made in the above-described constructions, without thereby departing from the spirit and scope of the present invention.

I claim:

1. A cryostat microtome apparatus comprising a cooling enclosure; a microtome mounted in said enclosure, refrigeration means operatively connected to said enclosure for cooling the same; a base positioned below said enclosure; support means for providing a vertically adjustable connection between said enclosure and said base, said support means including a plurality of parallel, vertical members and a plurality of guide members each of said guide members operatively engaging a respective vertical member; said vertical members being mounted on said base and said guide members being mounted on said enclosure.

2. The apparatus according to claim 1 wherein said base is a right-angled quadrangular frame.

3. Apparatus as set forth in claim 2 wherein at least two of said support members include a rotatably-mounted threaded spindle, the respective guide members include an internally threaded sleeve and drive means for rotating said spindles whereby the height of said enclosure can be varied.

4. Apparatus as set forth in claim 3 wherein there are four spindles and four sleeves.

5. Apparatus as set forth in claim 2 wherein at least two of said support members each include a toothed rack extending in a vertical direction, the respective guide means include rotary gears operatively engaging a respective rack and drive means for driving said gears in rotation, to vary the height of said enclosure.

6. Apparatus as set forth in claim 5 wherein there are four said support members each having a toothed rack and four respective said guide means each having a gear.

7. Apparatus as set forth in claim 6 wherein said drive means is reversible and rotates said four gears.

8. Apparatus as set forth in claim 1 wherein said support means include gas compression springs operatively disposed between said base and said enclosure, the force of said springs being greater than the mass of said enclosure.

9. Apparatus as set forth in claim 8 further including lock means for releasably retaining the enclosure at a chosen height.

* * * * *